(12) United States Patent
Chen

(10) Patent No.: US 9,089,268 B2
(45) Date of Patent: Jul. 28, 2015

(54) NEURAL SENSING DEVICE AND METHOD FOR MAKING THE SAME

(71) Applicant: Advanced Semiconductor Engineering, Inc., Kaohsiung (TW)

(72) Inventor: Kuo-Hua Chen, Kaohsiung (TW)

(73) Assignee: Advanced Semiconductor Engineering, Inc. (TW)

( * ) Notice: Subject to any disclaimer, the term of this patent is extended or adjusted under 35 U.S.C. 154(b) by 171 days.

(21) Appl. No.: 13/802,355

(22) Filed: Mar. 13, 2013

(65) Prior Publication Data

US 2014/0275911 A1 Sep. 18, 2014

(51) Int. Cl.
*A61B 5/0478* (2006.01)
*A61B 5/04* (2006.01)
*H01L 21/768* (2006.01)
*A61B 5/00* (2006.01)

(52) U.S. Cl.
CPC ........... *A61B 5/04001* (2013.01); *A61B 5/0478* (2013.01); *A61B 5/685* (2013.01); *A61B 5/6868* (2013.01); *H01L 21/76898* (2013.01); *A61B 2562/046* (2013.01); *A61B 2562/12* (2013.01)

(58) Field of Classification Search
CPC .. A61B 5/04001; A61B 5/0478; A61B 5/685; A61B 5/6868; A61B 2562/046
USPC .............................. 600/373, 377, 378; 607/116
See application file for complete search history.

(56) References Cited

U.S. PATENT DOCUMENTS

| | | |
|---|---|---|
| 3,761,782 A | 9/1973 | Youmans |
| 4,394,712 A | 7/1983 | Anthony |
| 4,499,655 A | 2/1985 | Anthony |
| 4,807,021 A | 2/1989 | Okumura |
| 4,842,699 A | 6/1989 | Hua et al. |
| 4,897,708 A | 1/1990 | Clements |
| 4,969,468 A * | 11/1990 | Byers et al. ................... 600/373 |
| 4,982,265 A | 1/1991 | Watanabe et al. |
| 5,166,097 A | 11/1992 | Tanielian |
| 5,191,405 A | 3/1993 | Tomita et al. |
| 5,215,088 A * | 6/1993 | Normann et al. ............. 600/377 |
| 5,229,647 A | 7/1993 | Gnadinger |
| 5,239,448 A | 8/1993 | Perkins et al. |
| 5,308,443 A | 5/1994 | Sugihara |
| 5,404,044 A | 4/1995 | Booth et al. |
| 5,615,477 A | 4/1997 | Sweitzer |
| 5,643,831 A | 7/1997 | Ochiai et al. |
| 5,969,238 A | 10/1999 | Fischer |
| 5,998,292 A | 12/1999 | Black et al. |
| 6,276,599 B1 | 8/2001 | Ogawa |
| 6,329,631 B1 | 12/2001 | Yueh |
| 6,406,934 B1 | 6/2002 | Glenn et al. |

(Continued)

FOREIGN PATENT DOCUMENTS

| | | |
|---|---|---|
| JP | 2002246540 A | 8/2002 |
| JP | 2004228135 A | 8/2004 |
| TW | 200612539 A | 4/2006 |

*Primary Examiner* — Lee S Cohen

(74) *Attorney, Agent, or Firm* — Morgan Law Offices, PLC

(57) ABSTRACT

The present invention provides a neural sensing device and method for making the same. The neural sensing device includes a base, an integrated circuit portion and a plurality of microprobes. The base has an active surface and a backside surface. The integrated circuit portion is disposed on the active surface of the base. The microprobes protrude from the backside surface of the base. The conductive vias are disposed in the microprobes and electrically connected to the integrated circuit portion.

12 Claims, 13 Drawing Sheets

(56) References Cited

U.S. PATENT DOCUMENTS

| | | |
|---|---|---|
| 6,448,506 B1 | 9/2002 | Glenn et al. |
| 6,457,633 B1 | 10/2002 | Takashima et al. |
| 6,511,463 B1 * | 1/2003 | Wood et al. .................. 604/272 |
| 6,577,013 B1 | 6/2003 | Glenn et al. |
| 6,670,269 B2 | 12/2003 | Mashino |
| 6,699,787 B2 | 3/2004 | Mashino |
| 6,740,950 B2 | 5/2004 | Paek |
| 6,812,549 B2 | 11/2004 | Umetsu et al. |
| 6,815,348 B2 | 11/2004 | Mashino |
| 6,962,829 B2 | 11/2005 | Glenn et al. |
| 7,078,269 B2 | 7/2006 | Yamasaki et al. |
| 7,134,198 B2 | 11/2006 | Nakatani |
| 7,157,372 B1 | 1/2007 | Trezza |
| 7,215,032 B2 | 5/2007 | Trezza |
| 7,222,420 B2 | 5/2007 | Moriizumi |
| 7,238,590 B2 | 7/2007 | Yang et al. |
| 7,262,475 B2 | 8/2007 | Kwon et al. |
| 7,276,787 B2 | 10/2007 | Edelstein et al. |
| 7,285,434 B2 | 10/2007 | Yee et al. |
| 7,298,030 B2 | 11/2007 | McWilliams et al. |
| 7,334,326 B1 | 2/2008 | Huemoeller et al. |
| 7,365,436 B2 | 4/2008 | Yamano |
| 7,368,305 B2 | 5/2008 | van der Weide et al. |
| 7,371,602 B2 | 5/2008 | Yee |
| 7,388,293 B2 | 6/2008 | Fukase et al. |
| 7,415,762 B2 | 8/2008 | Fukase et al. |
| 7,429,333 B2 | 9/2008 | Chiou et al. |
| 7,482,272 B2 | 1/2009 | Trezza |
| 7,508,057 B2 | 3/2009 | Shiraishi et al. |
| 7,508,079 B2 | 3/2009 | Higashi |
| 7,528,053 B2 | 5/2009 | Huang et al. |
| 7,538,033 B2 | 5/2009 | Trezza |
| 7,553,752 B2 | 6/2009 | Kuan et al. |
| 7,560,744 B2 | 7/2009 | Hsiao et al. |
| 7,598,163 B2 | 10/2009 | Callahan et al. |
| 7,605,463 B2 | 10/2009 | Sunohara |
| 7,625,818 B2 | 12/2009 | Wang |
| 7,642,132 B2 | 1/2010 | Huang et al. |
| 7,656,023 B2 | 2/2010 | Sunohara et al. |
| 7,659,202 B2 | 2/2010 | Trezza |
| 7,666,711 B2 | 2/2010 | Pagaila et al. |
| 7,678,685 B2 | 3/2010 | Sunohara et al. |
| 7,681,779 B2 | 3/2010 | Yang |
| 7,687,397 B2 | 3/2010 | Trezza |
| 7,691,747 B2 | 4/2010 | Lin et al. |
| 7,733,661 B2 | 6/2010 | Kossives et al. |
| 7,741,148 B1 | 6/2010 | Marimuthu et al. |
| 7,741,152 B2 | 6/2010 | Huang et al. |
| 7,741,156 B2 | 6/2010 | Pagaila et al. |
| 7,772,081 B2 | 8/2010 | Lin et al. |
| 7,772,118 B2 | 8/2010 | Yamano |
| 7,786,008 B2 | 8/2010 | Do et al. |
| 7,786,592 B2 | 8/2010 | Trezza |
| 7,795,140 B2 | 9/2010 | Taguchi et al. |
| 7,808,060 B2 | 10/2010 | Hsiao |
| 7,808,111 B2 | 10/2010 | Trezza |
| 7,811,858 B2 | 10/2010 | Wang et al. |
| 7,816,265 B2 | 10/2010 | Wang |
| 7,842,597 B2 | 11/2010 | Tsai |
| 7,875,479 B2 | 1/2011 | Chiou et al. |
| 7,941,201 B2 * | 5/2011 | Chiou et al. .................. 600/373 |
| 7,991,475 B1 * | 8/2011 | Tang et al. ....................... 607/45 |
| 8,639,312 B2 * | 1/2014 | Clark et al. .................... 600/378 |
| 2002/0017855 A1 | 2/2002 | Cooper et al. |
| 2002/0094605 A1 | 7/2002 | Pai et al. |
| 2004/0006264 A1 * | 1/2004 | Mojarradi et al. ............ 600/378 |
| 2004/0054393 A1 * | 3/2004 | Stemme et al. ................ 607/149 |
| 2004/0124518 A1 | 7/2004 | Karnezos |
| 2004/0259292 A1 | 12/2004 | Beyne et al. |
| 2005/0189635 A1 | 9/2005 | Humpston et al. |
| 2005/0258545 A1 | 11/2005 | Kwon |
| 2006/0027632 A1 | 2/2006 | Akram |
| 2006/0197216 A1 | 9/2006 | Yee |
| 2007/0048896 A1 | 3/2007 | Andry et al. |
| 2007/0138562 A1 | 6/2007 | Trezza |
| 2007/0187711 A1 | 8/2007 | Hsiao et al. |
| 2008/0272486 A1 | 11/2008 | Wang et al. |
| 2009/0032928 A1 | 2/2009 | Chiang et al. |
| 2009/0039527 A1 | 2/2009 | Chan et al. |
| 2009/0140436 A1 | 6/2009 | Wang |
| 2009/0146297 A1 | 6/2009 | Badakere et al. |
| 2009/0166785 A1 | 7/2009 | Camacho et al. |
| 2009/0243045 A1 | 10/2009 | Pagaila et al. |
| 2009/0294959 A1 | 12/2009 | Chiang et al. |
| 2009/0302435 A1 | 12/2009 | Pagaila et al. |
| 2009/0302437 A1 | 12/2009 | Kim et al. |
| 2009/0309235 A1 | 12/2009 | Suthiwongsunthorn et al. |
| 2009/0321916 A1 | 12/2009 | Wang et al. |
| 2010/0059855 A1 | 3/2010 | Lin et al. |
| 2010/0065948 A1 | 3/2010 | Bae et al. |
| 2010/0133704 A1 | 6/2010 | Marimuthu et al. |
| 2010/0140737 A1 | 6/2010 | Lin et al. |
| 2010/0140751 A1 | 6/2010 | Tay et al. |
| 2010/0140752 A1 | 6/2010 | Marimuthu et al. |
| 2010/0140776 A1 | 6/2010 | Trezza |
| 2010/0148316 A1 | 6/2010 | Kim et al. |
| 2010/0187681 A1 | 7/2010 | Chen et al. |
| 2010/0197134 A1 | 8/2010 | Trezza |
| 2010/0230759 A1 | 9/2010 | Yang et al. |
| 2010/0230760 A1 | 9/2010 | Hung |
| 2010/0230788 A1 | 9/2010 | Peng |
| 2010/0244244 A1 | 9/2010 | Yang |
| 2010/0276690 A1 | 11/2010 | Chen |
| 2010/0327465 A1 | 12/2010 | Shen et al. |
| 2011/0048788 A1 | 3/2011 | Wang et al. |
| 2011/0068437 A1 | 3/2011 | Chiu et al. |

* cited by examiner

NEURAL SENSING DEVICE AND METHOD FOR MAKING THE SAME

BACKGROUND OF THE INVENTION

1. Field of the Invention

The present invention relates to neurological diagnostic and therapeutic medical devices, and, more particularly, to a neural sensing device with a plurality of microprobes useful for collecting bio-electrical signals and a method for making the same.

2. Description of the Related Art

Conventional neural sensing devices for use in recording and measuring electrical activity of the brain, such as those used in electroencephalography (EEG), include a plurality of microprobes, each having a metal needle or a needle coated with a metal layer. The microprobes are utilized to penetrate the skin of the scalp to collect bio-electrical signals from a patient.

Skin is a layered structure, including two primary layers: the epidermis, which provides waterproofing and serves as a barrier to infection; and the dermis, which serves as a location for the appendages of the skin. The epidermis can be roughly divided into another two layers: the stratum corneum and the stratum germinativum. The stratum corneum includes dead skin cells, and, therefore serves as a waterproof barrier layer. The stratum germinativum comprises living cells and provides good electrical conductivity. Unfortunately, conventional neural sensing devices tend to be affected by undesired noise through the portions of the microprobes in the stratum corneum.

SUMMARY OF THE INVENTION

One aspect of the disclosure relates to a neural sensing device. In one embodiment, the neural sensing device includes a base having an active surface and a backside surface; an integrated circuit portion disposed on the active surface of the base; and a plurality of microprobes protruding from the backside surface of the base, each of the microprobes having a conductive via disposed therein and electrically connected to the integrated circuit portion. Each of the conductive vias penetrates through the base and the respective microprobe, extending from the active surface of the base to a tip of the microprobe. The conductive vias are electrically isolated from each other. In an embodiment, a circular insulation material surrounds conductive metal of each of the conductive vias. In an embodiment, the base and the microprobes are made of the same semiconductor material, e.g., silicon.

The integrated circuit portion comprises at least one electrical element, a plurality of metal layers and at least one dielectric layer, the at least one electrical element is disposed adjacent to the active surface of the base and covered by the dielectric layer, and the metal layers are embedded in the dielectric layer. Each of the microprobes has a probe body and an isolation layer, wherein the probe body protrudes from the backside surface of the base, the conductive via penetrates through the probe body, and the isolation layer covers the probe body and has an opening to expose a tip of the conductive via. The exposed tip can be plated with platinum which is considered safe for humans. In operation, the microprobes are used to penetrate the stratum germinativum layer of human skin to collect bio-signals via the exposed tips of the conductive vias. When the stratum germinativum layer is penetrated, the microprobes are electrically insulated from the stratum corneum layer of the skin by the isolation layer, thus reducing noise.

In an embodiment, the neural sensing device further comprises a plurality of redistribution layers electrically connecting the integrated circuit portion and the conductive via; at least one protection layer covering the redistribution layers; and a plurality of under bump metallurgies (UBMs) disposed on the protection layer and electrically connected to the redistribution layers. In this embodiment, a tip of each of the conductive vias is exposed from the active surface of the base, and each of the redistribution layers contacts the exposed tip of each of the conductive vias. In an embodiment, the integrated circuit portion comprises a plurality of bottommost pads disposed on the active surface of the base, wherein a tip of each of the conductive vias is exposed from the active surface of the base, and each of the bottommost pads contacts the exposed tip of each of the conductive vias.

Another aspect of the disclosure relates to a method of making a neural sensing device. In one embodiment, a method for making a neural sensing device comprises the steps of (a) providing a wafer having a base and an integrated circuit portion disposed on an active surface of the base; (b) forming a plurality of conductive vias in the base from the active surface of the base, wherein the conductive vias are electrically connected to the integrated circuit portion; (c) thinning the base from a backside surface thereof to expose the conductive via; (d) selectively removing the base from a backside surface thereof to form a plurality of probe bodies, wherein each of the conductive vias is disposed in each of the probes; and (e) dicing the wafer to form a plurality of neural sensing devices. Step (b) can include (b1) forming a plurality of openings on the integrated circuit portion to expose the active surface of the base; (b2) forming the conductive via in the base from the active surface of the base according to the openings of the integrated circuit portion; and (b3) forming a plurality of redistribution layers to electrically connect the integrated circuit portion and the conductive vias. In (b3), the redistribution layers can extend into the openings of the integrated circuit portion to contact the conductive vias. In an embodiment, step (b2) includes (b21) forming a plurality of holes on the active surface of the base; (b22) forming a circular insulation material on a sidewall of each of the holes so as to define a central hole; and (b23) filling an conductive metal in the central hole. Step (b3) can include (b4) forming at least one protection layer to cover the redistribution layers; and (b5) forming a plurality of under bump metallurgies (UBMs) on the protection layer to electrically connect the redistribution layers. After step d), the method can include (d1) forming an isolation layer on the probe bodies and the backside surface of the base, wherein the isolation layer has a plurality of openings to expose the conductive vias; and (d2) forming a plurality of tip metals in the openings of the isolation layer to contact the conductive vias.

BRIEF DESCRIPTION OF THE DRAWINGS

Common reference numerals are used throughout the drawings and the detailed description to indicate the same elements. The present invention will be more apparent from the following detailed description taken in conjunction with the accompanying drawings.

DETAILED DESCRIPTION OF THE INVENTION

Figure 1:
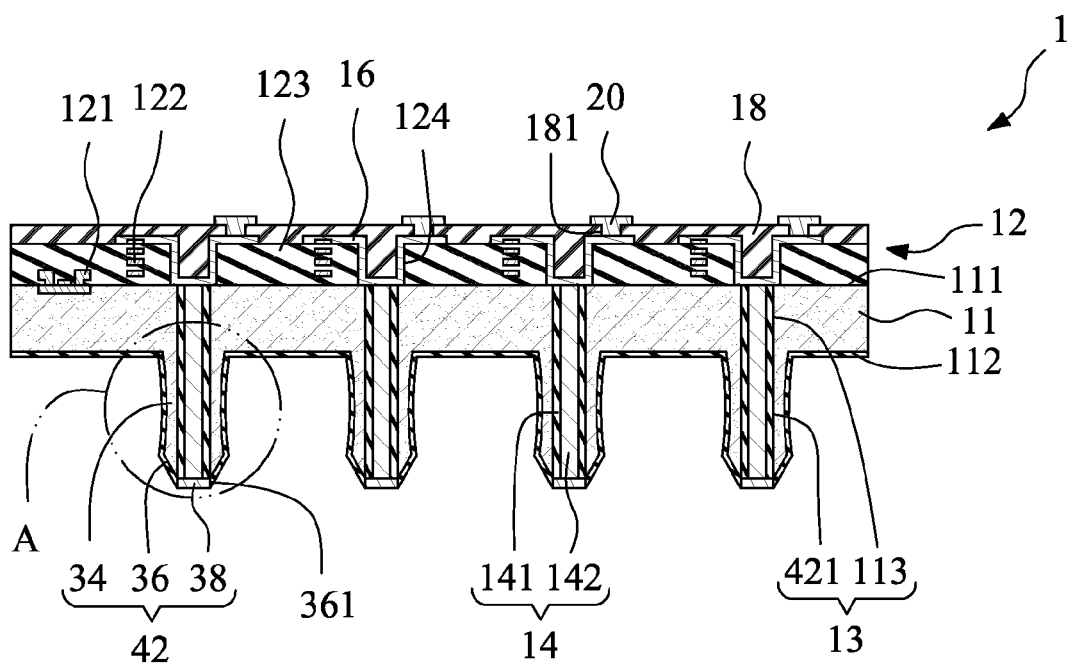
FIG. 1 illustrates a cross sectional view of a neural sensing device according to an embodiment of the present invention.

Referring to FIG. 1, a cross sectional view of a neural sensing device 1, according to an embodiment of the present invention, is illustrated. The neural sensing device 1 comprises a base 11, an integrated circuit portion 12, a plurality of conductive vias 14, a plurality of redistribution layers 16, a protection layer 18, a plurality of under bump metallurgies (UBMs) 20 and a plurality of microprobes 42.

The base 11 has an active surface 111, a backside surface 112 and a plurality of base holes 113. In this embodiment, the material of the base 11 is silicon.

The integrated circuit portion 12 is disposed on the active surface 111 of the base 11. In this embodiment, the integrated circuit portion 12 comprises at least one electrical element 121, a plurality of metal layers 122, at least one dielectric layer 123, and a plurality of openings 124.

The at least one electrical element 121 (which can include complementary metal-oxide-semiconductor (CMOS), micro-electro-mechanical systems (MEMS), simulators, controllers, RF telemetry, power receiving coil or an antenna, etc.) is disposed adjacent to the active surface 111 of the base 11 and covered by the dielectric layer 123. The metal layers 122 are covered by, and embedded in, the dielectric layer 123 and electrically connected to the electrical element 121. Usually, the integrated circuit portion 12 includes at least three metal layers 122. The upmost layer of the metal layers 122 is not covered by the dielectric layer 123. In this embodiment, the thickness of the base 11 is at least about 200 μm and the thickness of the integrated circuit portion 12 is about 10 to 20 μm. The openings 124 penetrate through the integrated circuit portion 12.

The microprobes 42 protrude from the backside surface 112 of the base 11. Each of the microprobes 42 comprises a probe body 34, an isolation layer 36, and a via hole 421. The probe body 34 protrudes from the backside surface 112 of the base 11. In this embodiment, the probe body 34 is formed from the base 11. Thus, the material of the probe body 34 is also silicon. The isolation layer 36 covers, and electrically insulates, the probe body 34 and the backside surface 112 of the base 11, and has an opening 361 to expose a tip of the conductive via 14 which is plated by a tip metal 38. The via hole 421 is communicated with the base hole 113 to form a hole 13. In this embodiment, the material of the isolation layer 36 is Parylene, the material of the tip metal 38 is platinum, and the thickness of the isolation layer 36 is about 1 to 2 μm.

Each of the conductive vias 14 is disposed in the hole 13 and electrically connected to the integrated circuit portion 12. That is, each of the conductive vias 14 is disposed in each of the microprobes 42, and penetrates through the base 11 and the length of the microprobe 42. In this embodiment, the conductive via 14 has a circular insulation material 141 and a conductive metal 142. The circular insulation material 141 is disposed on the sidewall of the base hole 113 and the side wall of the via hole 421 (i.e., the side wall of the hole 13), and defines a central hole. The conductive metal 142 is disposed in the central hole. In this embodiment, the material of the circular insulation material 141 is polyimide (PI), and the material of the conductive metal 142 is copper (Cu). The top end of the conductive metal 142 is exposed from the active surface 111 of the base 11; and the bottom end of the conductive metal 142 is exposed from the probe body 34 and plated by the tip metal 38. It is noted that the conductive vias 14 are electrically insulated from each other.

The redistribution layers 16 are disposed on the integrated circuit portion 12 to electrically connect the upmost layer of the metal layers 122, and, in the openings 124 of the integrated circuit portion 12, to electrically connect the conductive via 14. The protection layer 18 is disposed on the integrated circuit portion 12 to cover the redistribution layers 16, wherein the protection layer 18 has a plurality of openings 181 to expose a part of each of the redistribution layers 16. The under bump metallurgies (UBMs) 20 are disposed on the protection layer 18 and in the openings 181 to electrically connect the redistribution layers 16.

Figure 1A:
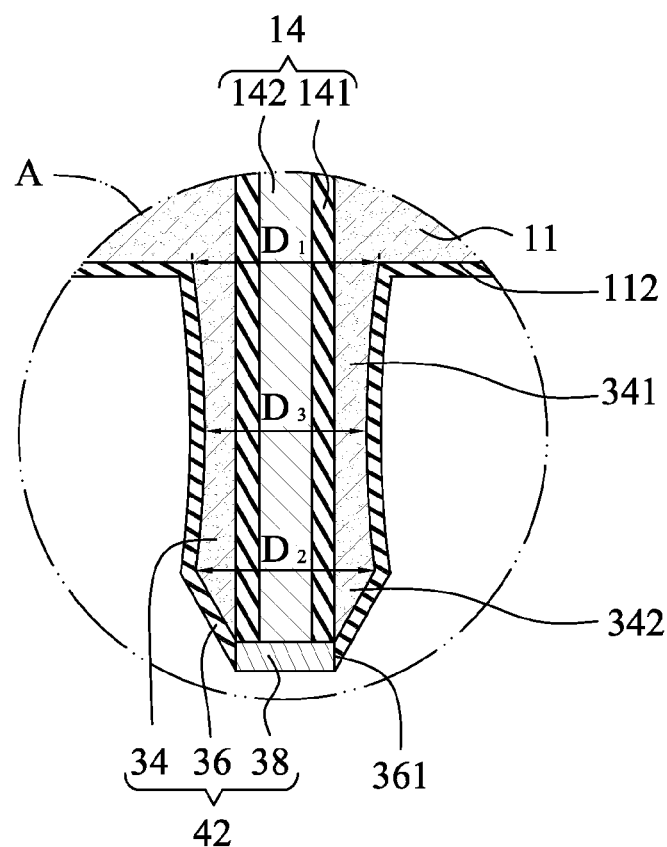
FIG. 1A illustrates a partially enlarged view of area A of FIG. 1.

Referring to FIG. 1A, a partially enlarged view of area A of FIG. 1 is illustrated. The probe body 34 has a main portion 341 and a tip portion 342 and the material of the probe body 34 is silicon. The part that the main portion 341 connects with the base 11 is defined as the first part, and the part that the main portion connects the tip portion 342 is defined as the second part. The diameter $D_1$ of the first part is greater than the diameter $D_2$ of the second part. In this embodiment, $D_1$ is about 1.1 to 5 times $D_2$. Furthermore, if the diameter $D_2$ is slightly smaller than the diameter $D_1$, the shear stress will be easier to release from the main portion 341 to the tip portion 342. Therefore, it is easier to penetrate through the stratum corneum (SC) into the stratum germinativum (SG) to collect bio-signals. In addition, since the diameter $D_1$ is greater than the diameter $D_2$, the probe body 34 is relatively firm and will not break easily. The narrowest part of the main portion 341 is defined as the third part, and the diameter $D_3$ of the third part is smaller than the diameter $D_2$ of the second part. In this embodiment, $D_3$ is about 0.5 to 1 times $D_2$. The third part is between the first part and the second part, so to form a recession. Therefore, when the microprobe 42 is inserted into the skin, it will be locked by the part of the skin that contacts the recession. It is noted that if the $D_3$ is less than 0.5 times $D_2$, the probe body 34 will break easily.

The probe body 34 is formed by selectively removing the base 11 by, e.g., etching. The main portion 341 is of a shape of a cylinder, and the tip portion 342 is in a shape of a needle. The isolation layer 36 is disposed on the probe bodies 34 and the backside surface 112 of the base 11 by physical vapor deposition (PVD). In this embodiment, the surface of the whole isolation layer 36 is continuously disposed on the probe bodies 34 along the main portion 341 and the tip portion 342 and has the opening 361 to expose a tip of the conductive via 14. The tip metal 38 is plated in the opening 361 of the isolation layer 36 to electrically connect the conductive metal 142. The material of the tip metal 38 is platinum which is not harmful to health and is safe to penetrate through the stratum corneum into the stratum germinativum.

The conductive via 14 is disposed in the microprobe 42, and penetrates through the base 11. In this embodiment, the bottom end of the conductive metal 142 is exposed from the tip portion 342 for collecting signals. As is well known, the signals from the human body, e.g., brain waves, are low-frequency analog signals which are relatively weak. However, in this embodiment, the signals of brain waves collected by the microprobes 42 can be transmitted to the integrated circuit portion 12 by the conductive vias 14, and then the electrical elements 121 will amplify the analog signals, and convert the amplified analog signals into digital signals. In order to ensure the signal transmission quality, the transmission path must be shortest to avoid noise interference.

In this embodiment, the conductive vias 14 can accomplish the above function, because the conductive vias 14 are disposed in each of the microprobes 42, so that signals collected by the conductive vias 14 in the microprobes 42 can be transmitted directly to the active surface 111 of the base 11 via the shortest transmission path. In addition, the conductive vias 14 are electrically insulated from each other so that different conductive via 14 may collect different signals; therefore, the resolution of sensing detection is high.

Figure 2:
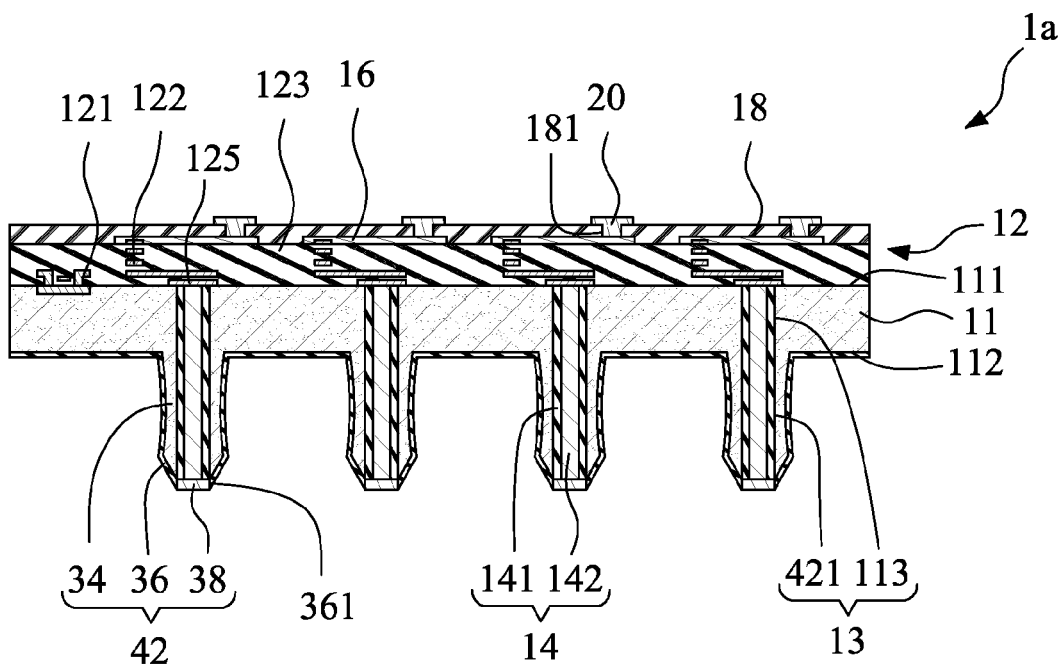
FIG. 2 illustrates a cross sectional view of a neural sensing device according to another embodiment of the present invention.

Referring to FIG. 2, a cross sectional view of a neural sensing device according to another embodiment of the present invention is illustrated. The neural sensing device 1a of this embodiment is substantially similar to the neural sensing device 1 of FIG. 1, and the difference between the neural sensing device 1a of this embodiment and the neural sensing device 1 of FIG. 1 is described as follows. The integrated circuit portion 12 further includes a plurality of bottommost pads 125 disposed on the active surface 111 of the base 11. Each of the bottommost pads 125 contacts the exposed tip of each of the conductive vias 14 and is electrically connected to the metal layers 122. That is, each of the conductive vias 14 extends to each of the bottommost pads 125. In this embodiment, the integrated circuit portion 12 dose not include the openings 124, and the redistribution layers 16 are disposed on the integrated circuit portion 12.

Figure 3:
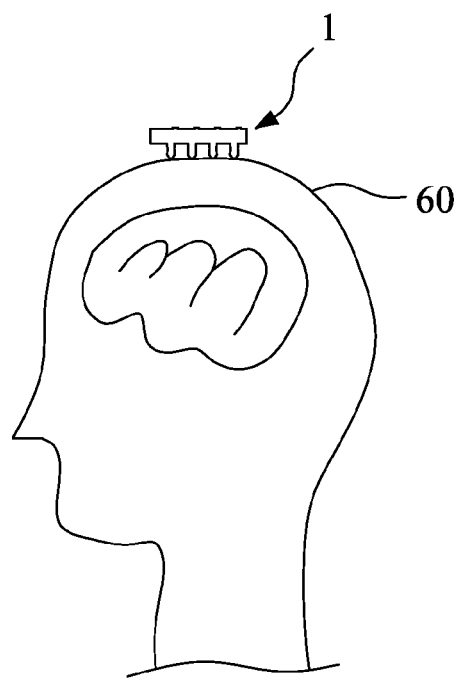
FIG. 3 illustrates an operation of the neural sensing device according to an embodiment of the present invention.

Referring to FIG. 3, an operation of the neural sensing device according to an embodiment of the present invention is illustrated. The neural sensing device 1 can be applied to collect the signals from human head 60, e.g., brain waves. Since the size of the neural sensing device 1 is vary small, the neural sensing device 1 can move with human body so that it is portable. In addition, the neural sensing device 1 can collect the signals from human head 60 by direct contact, thus, brain surgery is unnecessary. It is to be understood that the neural sensing device illustrated in FIG. 3 is not drawn to scale and that more than one such neural sensing device could be used simultaneously on a patient, along with other medical equipment, to capture and monitor electrical brain activity.

Figure 3A:
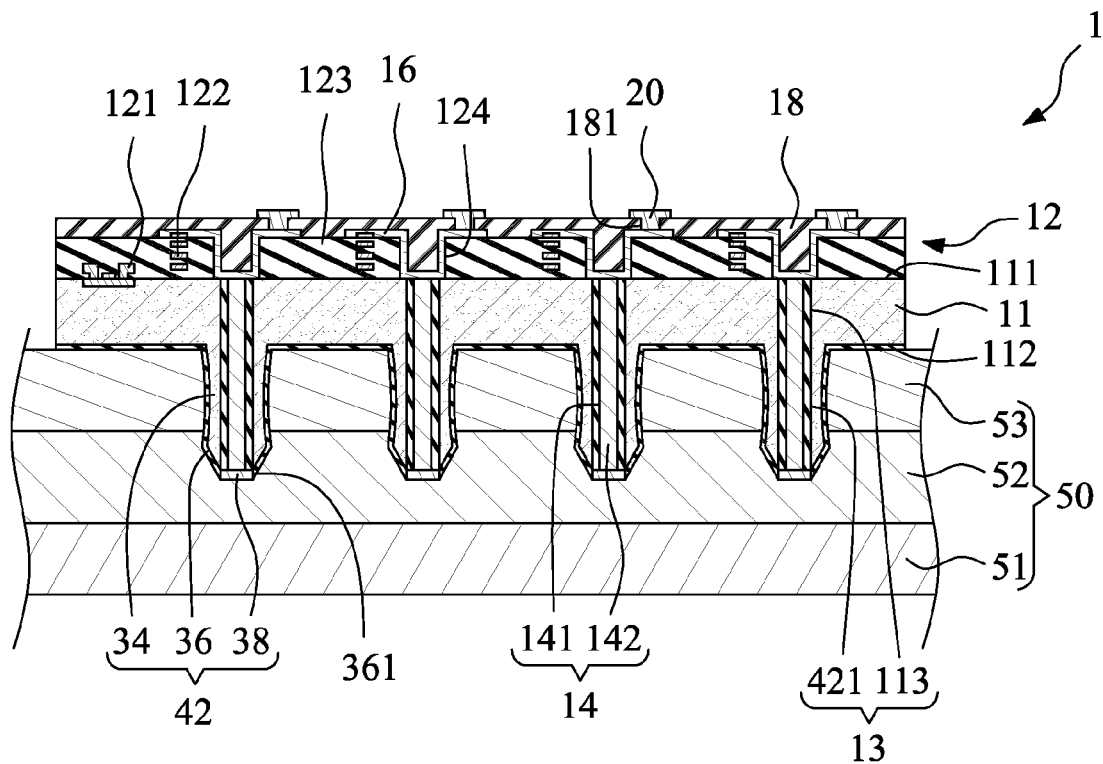
FIG. 3A illustrates an enlarged view of FIG. 3.

Referring to FIG. 3A, an enlarged view of FIG. 3 is illustrated. In order to collect the signals in the human body, the microprobes 42 of the neural sensing device 1 are inserted into the skin 50. As is well known, the skin 50 includes a dermis 51, a stratum germinativum (SG) 52, and a stratum corneum (SC) 53. Therefore, if the bio-signals in the stratum germinativum (SG) 52 are desired, the microprobes 42 must penetrate through the stratum corneum (SC) 53 and extend into the stratum germinativum (SG) 52 to collect the bio-signals. Since the portions of the microprobes 42 corresponding to the stratum corneum (SC) 53 are covered by the isolation layer 36, the measured result will not be affected by the undesired noises in the stratum corneum (SC) 53.

Furthermore, the bottom of the neural sensing device 1 is also covered by the isolation layer 36, the measured result will not be affected by the undesired noises from the surface of the skin 50, either. That is, only the exposed tip metals 38 in the stratum germinativum (SG) 52 can collect the bio-signals. The neural sensing device 1 of the present invention can be used, but not limited, to collect the following physiological signals with various frequency ranges: Electroencephalography (EEG) (0-100 Hz), Electrocorticography (ECoG) (0-200 Hz), Neural Spike (300-7 k Hz), Electrocardiogram (ECG) (0.05-1 kHz), Electromyogram (EMG) (0.01-10 kHz), and Electro-oculogram (EOG) (0-100 Hz). Thus, the neural sensing device 1 of the present invention can be used widely.

Figure 3B:
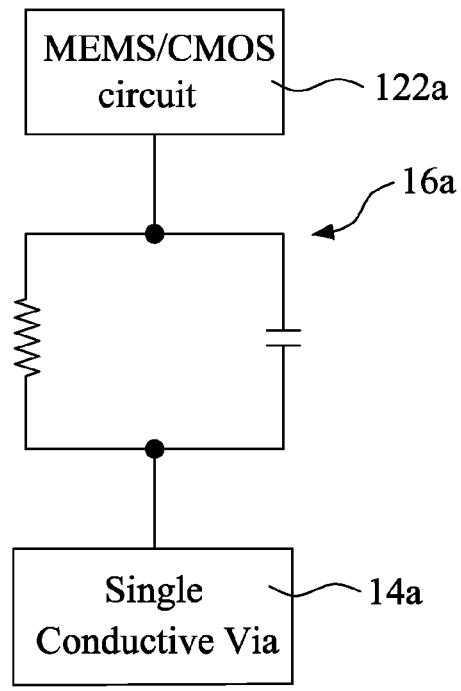
FIG. 3B illustrates a circuit diagram of a single conductive via of FIG. 3.

Referring to FIG. 3B, a circuit diagram of a single conductive via of FIG. 3A is illustrated. The single conductive via 14a corresponds to the conductive via 14 of FIG. 3A, the redistribution layer circuit 16a corresponds to the redistribution layer 16 of FIG. 3A, and the MEMS/CMOS circuit 122a corresponds to the electrical element 121 and the metal layer 122 of FIG. 3A. As shown, the signal collected by the single conductive via 14a is transmitted to the electrical element 121 through the redistribution layer circuit 16a and the MEMS/CMOS circuit 122a for further processing. Since the circuit of each conductive via 14 is independent from each other, the neural sensing device can be configured such that different conductive via 14 may collect different signals in different local areas; therefore, sensing detection resolution can be high.

Figure 4:
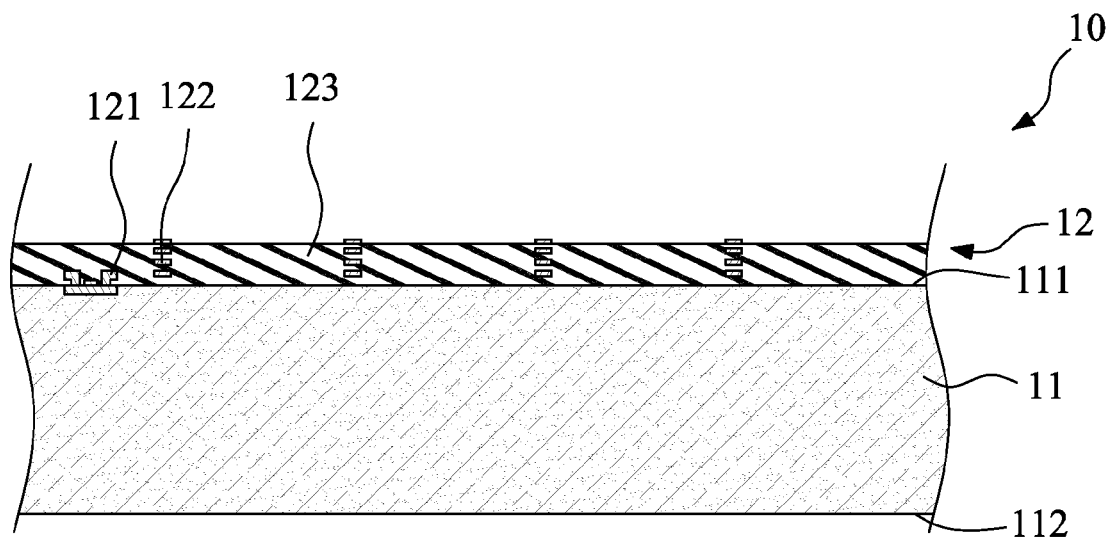
FIGS. 4 to 13 illustrate a method for making a neural sensing device according to an embodiment of the present invention.

Referring to FIGS. 4 to 13, a method for making a neural sensing device according to an embodiment of the present invention is illustrated. Referring to FIG. 4, a wafer 10 is provided. The wafer 10 has the base 11 and the integrated circuit portion 12. In this embodiment, the material of the base 11 is silicon, and the base 11 has the active surface 111 and the backside surface 112. The integrated circuit portion 12 is disposed on the active surface 111 of the base 11. In this embodiment, the integrated circuit portion 12 comprises the at least one electrical element 121, the plurality of metal layers 122 and the at least one dielectric layer 123. The electrical element 121, such as complementary metal-oxide-semiconductor (CMOS), micro-electro-mechanical systems (MEMS), simulators, controllers, RF telemetry, power receiving coil or an antenna, etc., are disposed adjacent to the active surface 111 of the base 11 and covered by the dielectric layer 123. The metal layers 122 are covered by the dielectric layer 123 and electrically connected to the electrical element 121; therefore, the metal layers 122 are embedded in the dielectric layer 123. The upmost layer of the metal layers 122 are not covered by the dielectric layer 123. In this embodiment, the thickness of the base 11 is at least 350 μm and the thickness of the integrated circuit portion 12 is at least 15 μm.

Figure 5:
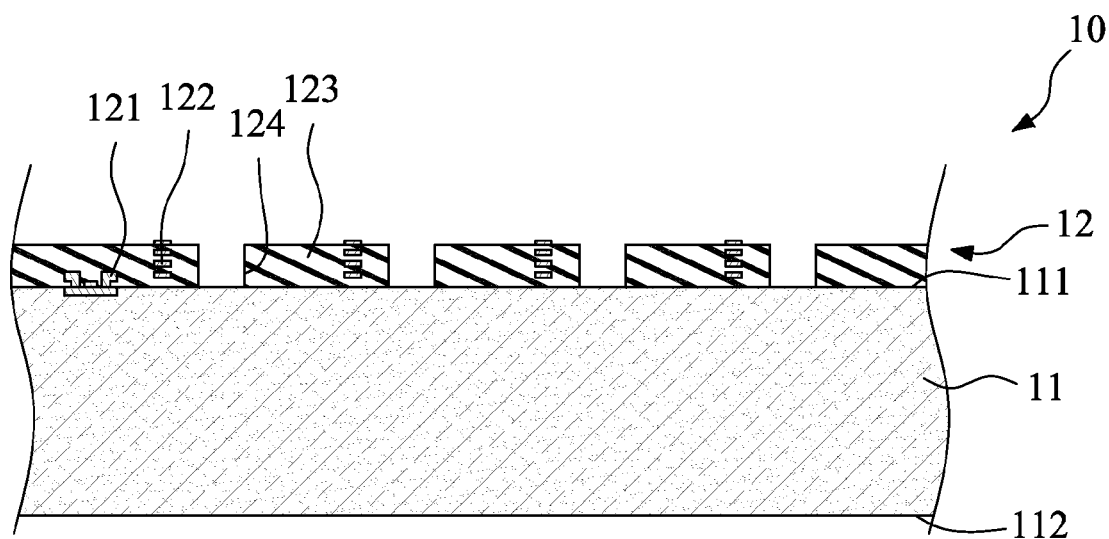

Referring to FIG. 5, a plurality of openings 124 is formed to penetrate through the integrated circuit portion 12 and expose a part of the active surface 111 of the base 11.

Figure 6:
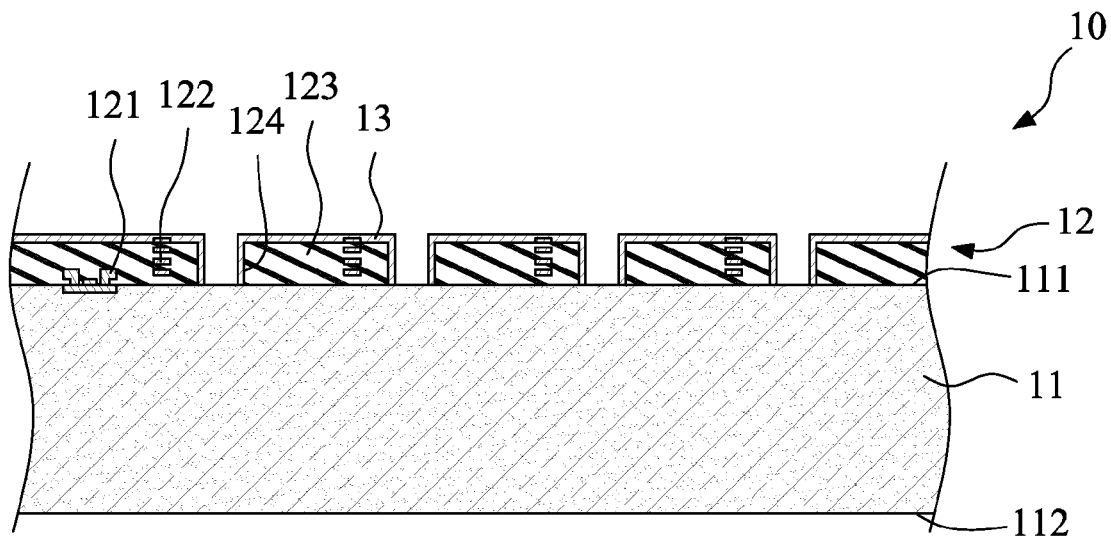

Referring to FIG. 6, a photoresist layer 13 is formed on the integrated circuit portion 12 and the sidewall of the openings 124. Then, the photoresist layer 13 that is disposed at the bottom of the openings 124 is removed so that the part of the active surface 111 of the base 11 is exposed.

Figure 7:
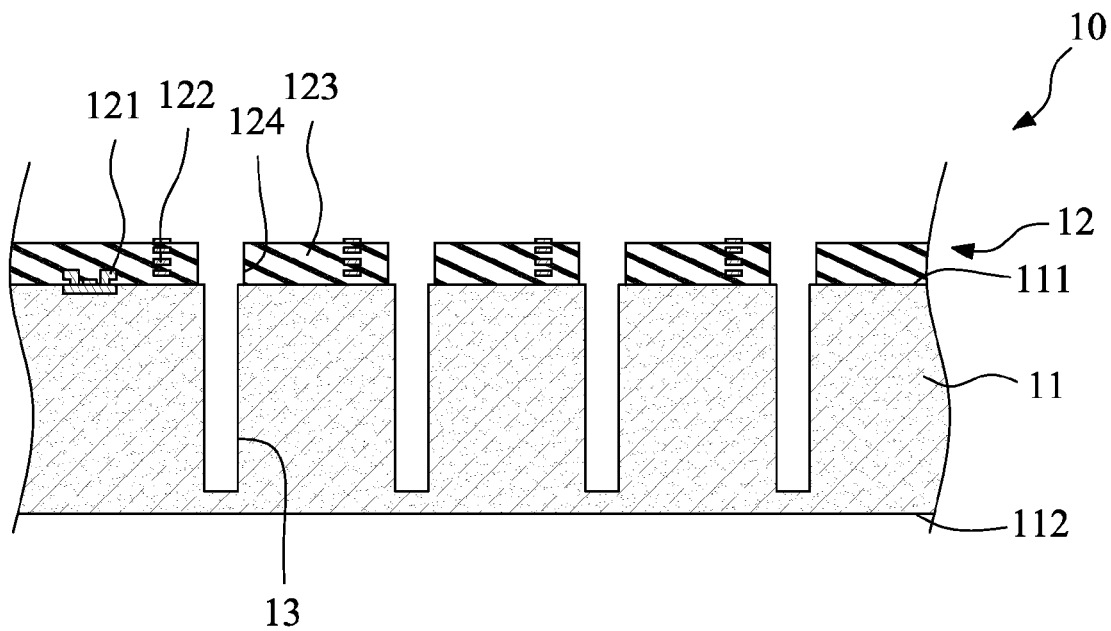

Referring to FIG. 7, the plurality of holes 13 are formed on the exposed part of the active surface 111 of the base 11 by, for example, dry etching, according to the openings 124. In this embodiment, each of the holes 13 is a blind hole that does not penetrate through the base 11. The holes 13 are communicated with the openings 124, and the diameter of the hole 13 is smaller than that of the opening 124. In this embodiment, the depth of the hole 13 is about 240 μm to 280 μm, and the diameter of the hole 13 is about 60 μm. Then, the photoresist layer 13 is released.

Figure 8:
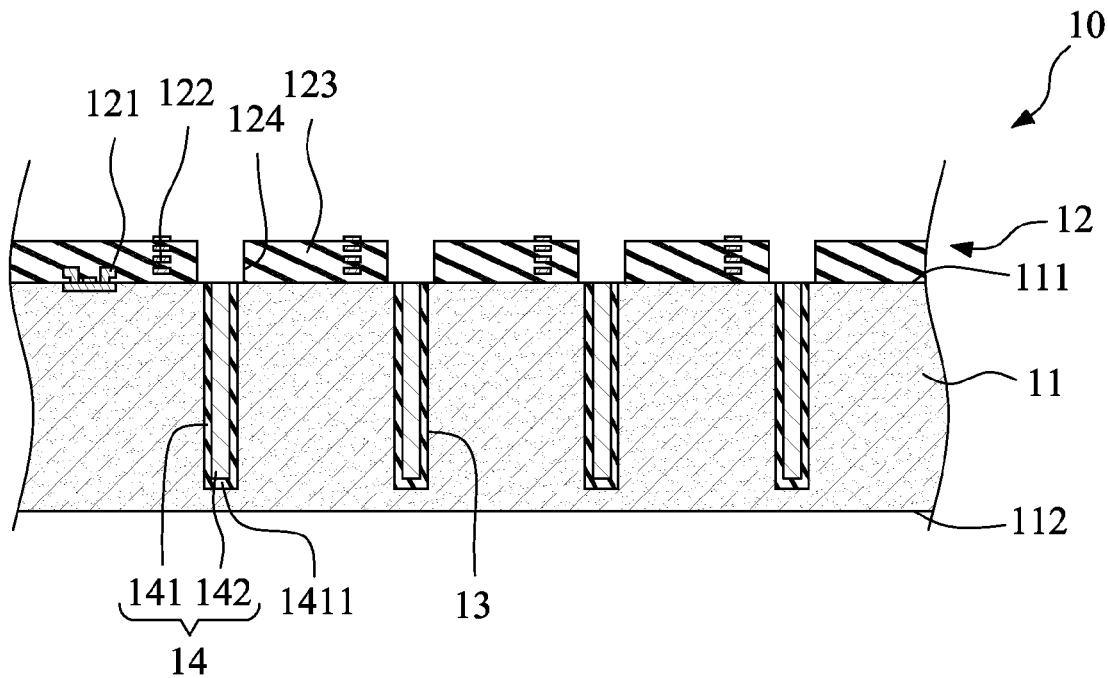

Referring to FIG. 8, the circular insulation material 141 is formed on the sidewall of the hole 13 so as to define a central hole. The circular insulation material 141 has a bottom portion 1411. Then, a conductive metal 142 fills in the central hole so as to form a conductive via 14. In this embodiment, the material of the circular insulation material 141 is $SiO_x$, and the material of the conductive metal 142 is copper (Cu).

Figure 9:
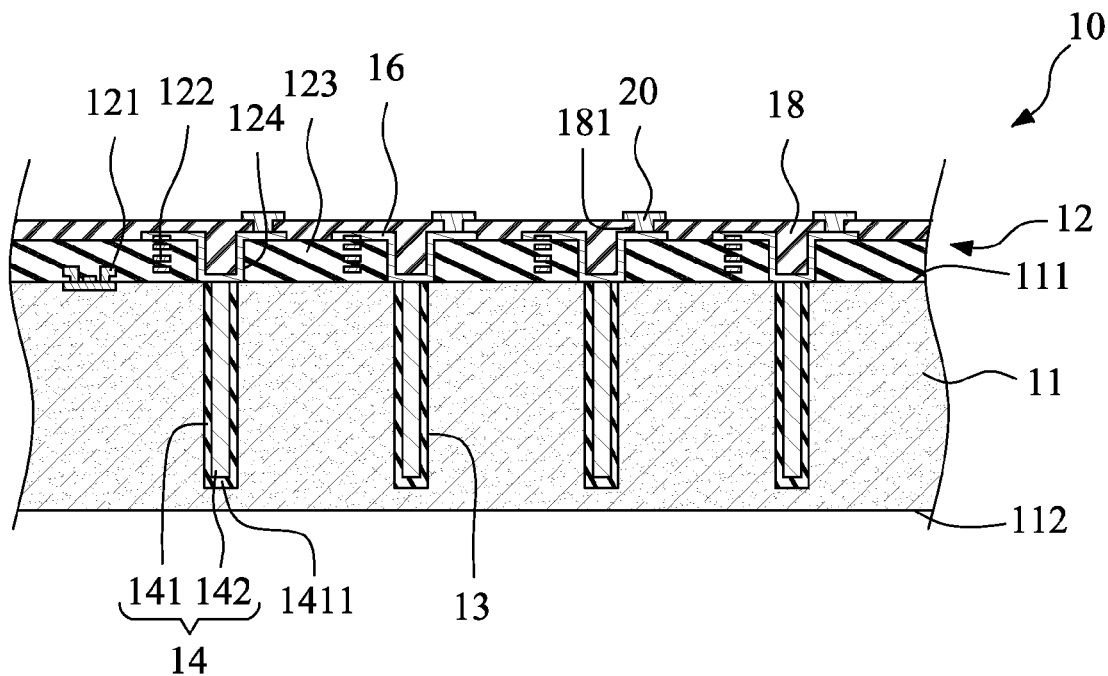

Referring to FIG. 9, a plurality of the redistribution layers 16 are formed on the integrated circuit portion 12 to electrically connect the upmost layer of the metal layers 122, and in the openings 124 of the integrated circuit portion 12 to electrically connect the conductive vias 14. Then, the protection layer 18 is formed on the integrated circuit portion 12 to cover the first redistribution layers 16, and in the openings 124, wherein the protection layer 18 has a plurality of openings 181 to expose a part of each of the redistribution layers 16. Then, the plurality of under bump metallurgies (UBMs) 20 are formed on the protection layer 18 and in the openings 181 to electrically connect the redistribution layers 16.

Figure 10:
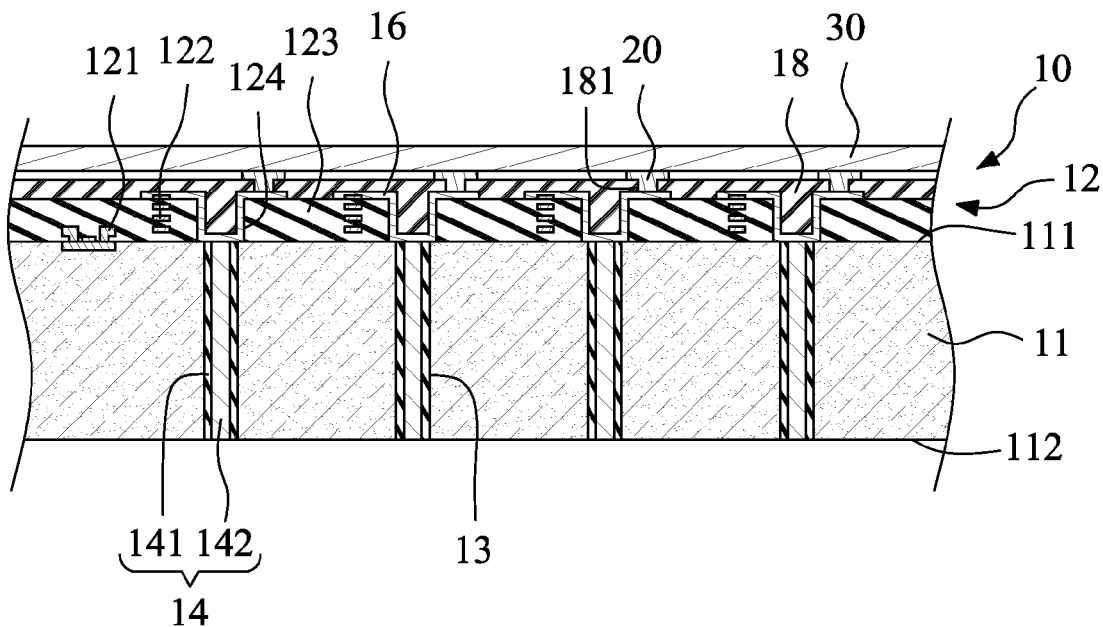

Referring to FIG. 10, the wafer 10 is attached to a carrier 30, wherein the under bump metallurgies (UBMs) 20 contacts the carrier 30. Then, the base 11 is thinned from the backside surface 112 thereof by grinding. Meanwhile, the bottom portion 1411 of the circular insulation material 141 is removed so as to expose the conductive metal 142 of the conductive via 14, and the conductive via 14 becomes a through silicon via (TSV).

Figure 11:
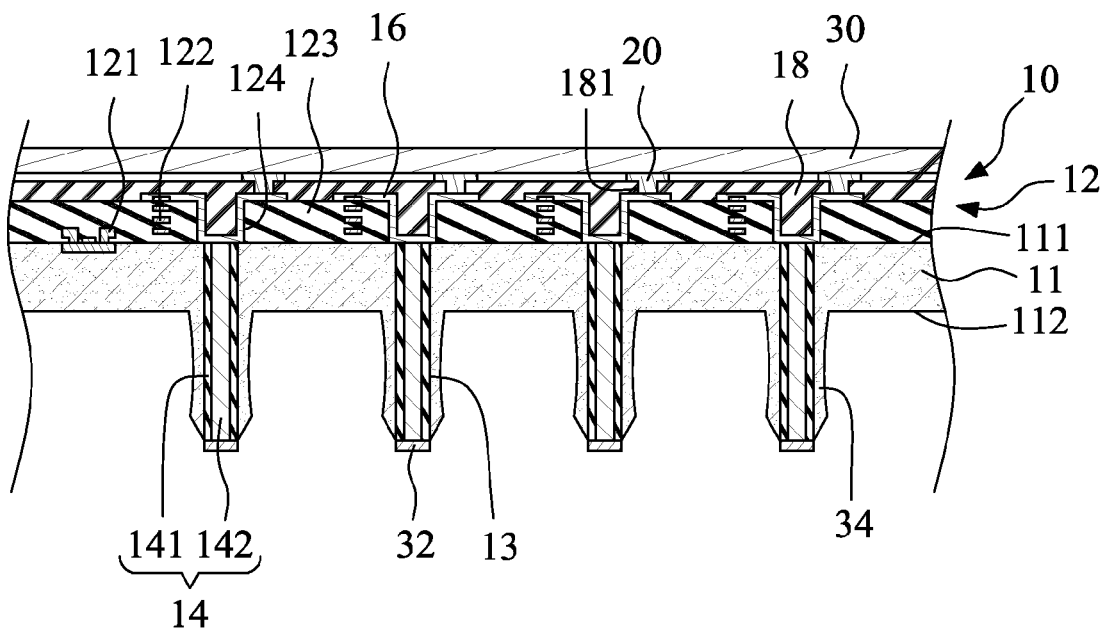

Referring to FIG. 11, a hard mask 32 is applied to the backside surface 112 of the base 11. The hard mask 32 has a pattern to cover the exposed conductive metal 142 of the conductive via 14, so that a part of the backside surface 112 of the base 11 is exposed. Then, the base 11 is selectively removed from the backside surface 112 by, for example, etching. That is, the exposed part of the backside surface 112 that is not covered by the hard mask 32 is removed by, e.g., by etching. Therefore, a plurality of needle-like probe bodies 34 are formed from the base 11 and protrude from the backside surface 112 of the base 11. Each of the conductive vias 14 is disposed in each of the probe bodies 34. In this embodiment, the height of the probe body 34 is at least about 150 μm, and the thickness of the remaining base 11 is at least about 200 μm.

Figure 12:
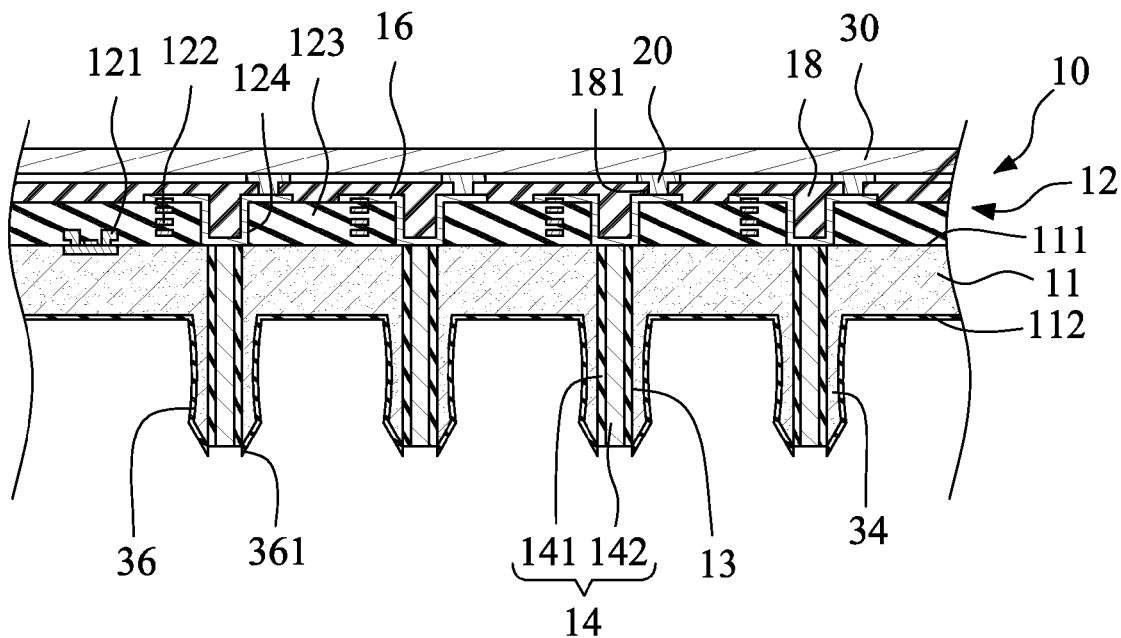

Referring to FIG. 12, the hard mask 32 is released so that the bottom end of the conductive metal 142 is exposed from the probe body 34. Then, the isolation layer 36 is formed on the probe bodies 34 and the backside surface 112 of the base 11 by physical vapor deposition (PVD). In this embodiment, the material of the isolation layer 36 is Parylene, and the thickness of the whole first isolation layer 36 is even. The thickness of the isolation layer 36 is about 1 μm to 2 μm. In order to make the isolation layer 36 have an even thickness, the processing condition is described as follows. The viscosity of the Parylene solution is determined that the ratio of the weight of Parylene to the weight of solvent is 1:1. The spray speed may be about 40 to 60 rpm. The spraying step is repeated four or five times to form the isolation layer 36 having the proper even thickness.

Then, a photoresist layer (not shown) is formed on the isolation layer 36. The photoresist layer has a plurality of openings corresponding to the conductive vias 14 so that a part of the isolation layer 36 is exposed. Then, the exposed part of the isolation layer 36 that is not covered by the photoresist layer is removed by, e.g., reactive ion etching (RIE). Therefore, the isolation layer 36 has an opening 361 to expose the conductive metal 142 of the conductive via 14. Then, the photoresist layer is released.

Figure 13:
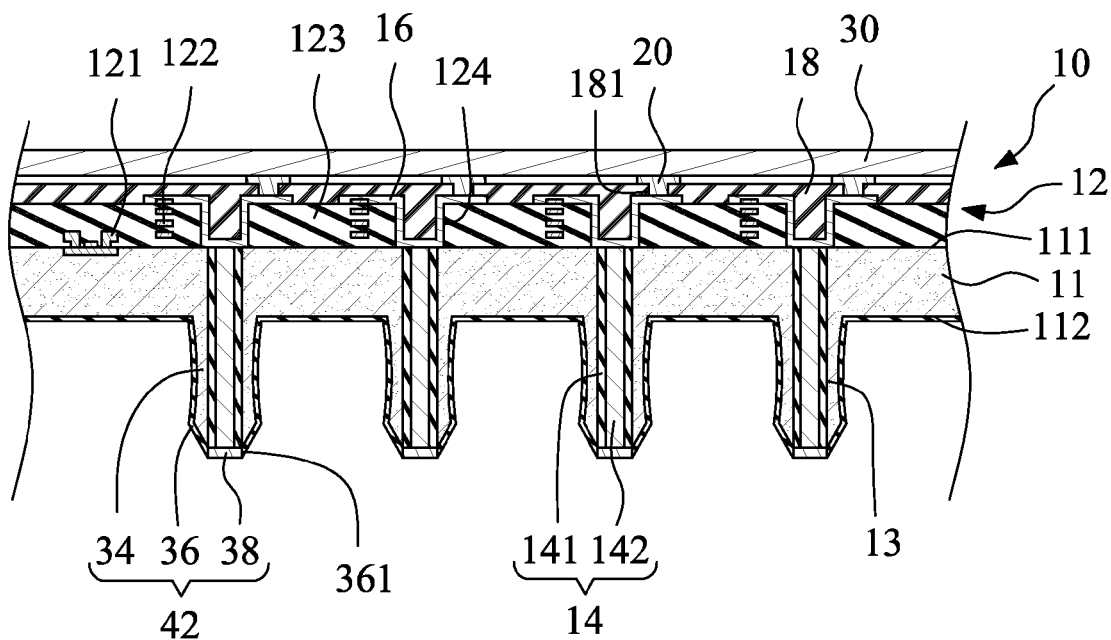

Referring to FIG. 13, a plurality of tip metals 38 are formed in the opening 361 of the isolation layer 36 by plating. Therefore, each of the tip metals 38 is formed on the conductive metal 142 of the conductive via 14, so as to contact the conductive metal 142 of the conductive via 14. In this embodiment, the material of the tip metal 38 is platinum.

Then, the wafer 10 is released from the carrier 30, and then attached to a dicing tape (not shown). Then, the wafer 10 and the dicing tape are diced. Then, the dicing tape is stripped so as to form a plurality of neural sensing devices 1 as shown in FIG. 1.

Referring to FIGS. 14 to 17, a method for making a neural sensing device according to another embodiment of the present invention is illustrated. The initial steps of the method of this embodiment are the same as the steps of FIGS. 4 and 5.

Figure 14:
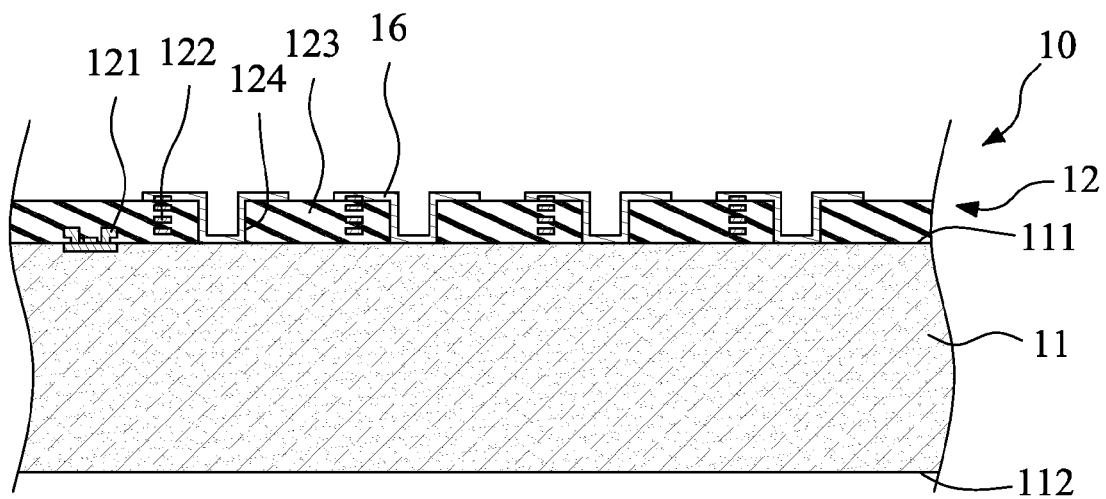
FIGS. 14 to 17 illustrate a method for making a neural sensing device according to another embodiment of the present invention.

Referring to FIG. 14, the redistribution layers 16 are formed on the integrated circuit portion 12 to electrically connect the upmost layer of the metal layers 122, and in the openings 124.

Figure 15:
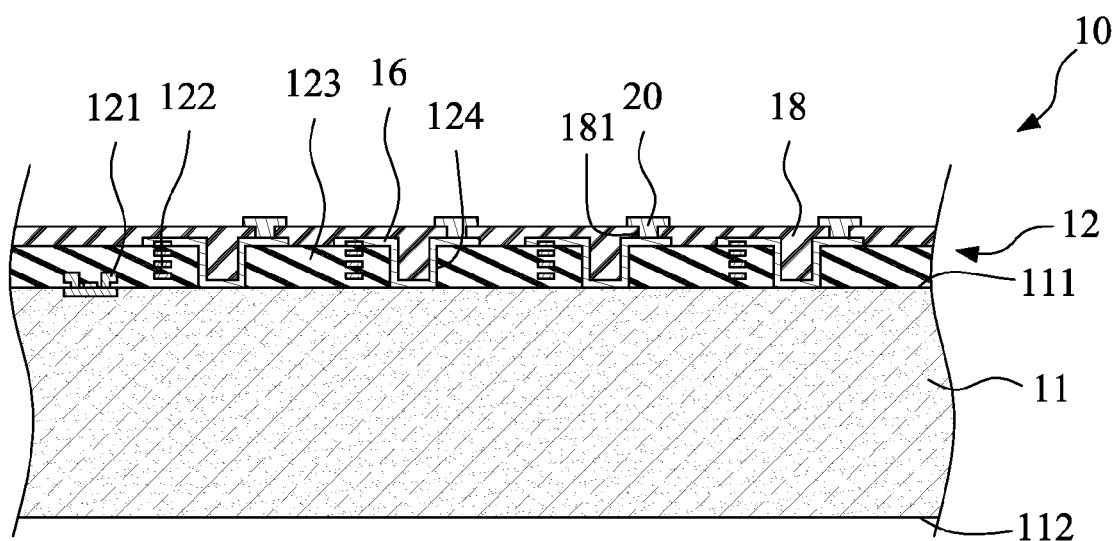

Referring to FIG. 15, the protection layer 18 is formed on the integrated circuit portion 12 to cover the first redistribution layers 16, and in the openings 124, wherein the protection layer 18 has a plurality of openings 181 to expose a part of each of the redistribution layers 16. Then, a plurality of under bump metallurgies (UBMs) 20 are formed on the protection layer 18 and in the openings 181 to electrically connect the redistribution layers 16.

Figure 16:
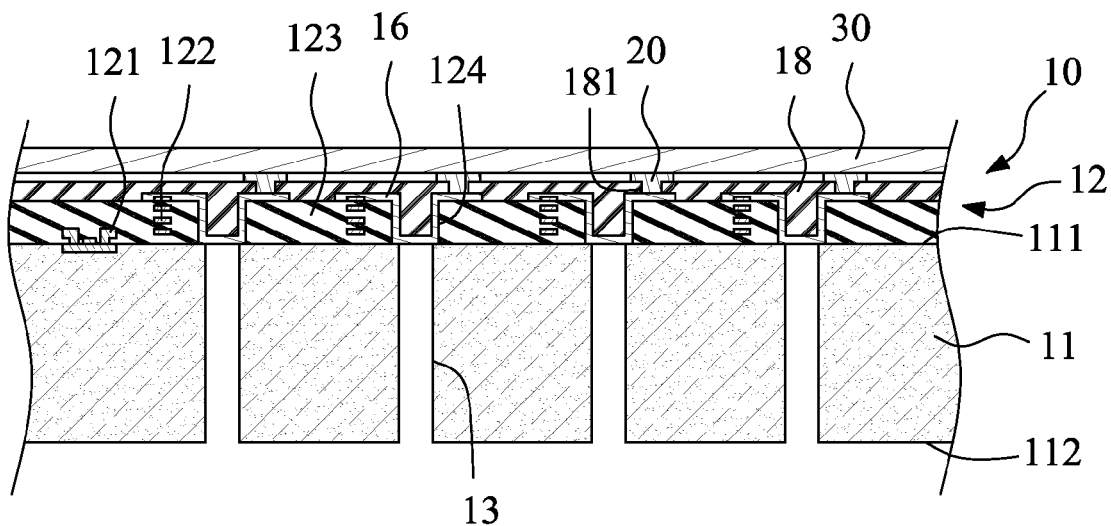

Referring to FIG. 16, the wafer 10 is attached to the carrier 30, wherein the under bump metallurgies (UBMs) 20 contacts the carrier 30. Then, the base 11 is thinned from the backside surface 112 thereof by grinding. Then, the holes 13 are formed in the base 11 from the backside surface 112 of the base 11 by, for example, dry etching. The positions of the holes 13 correspond to that of the openings 124 of the integrated circuit portion 12 so as to expose the redistribution layers 16. In this embodiment, the diameter of the hole 13 is smaller than that of the opening 124, the depth of the hole 13 is about 240 μm to 280 μm, and the diameter of the hole 13 is about 60 μm.

Figure 17:
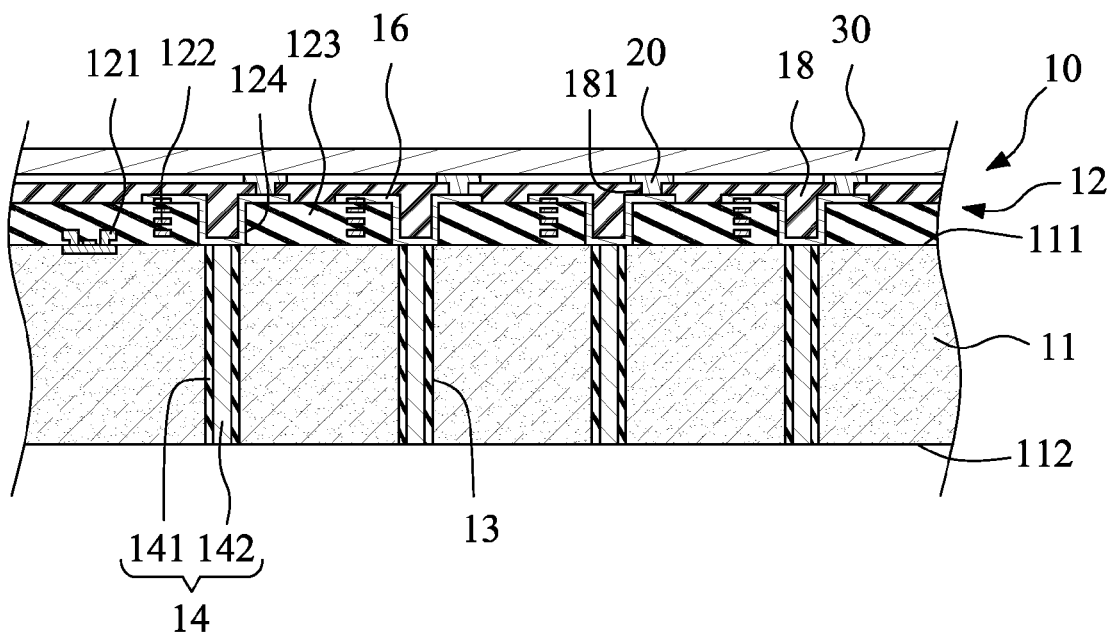

Referring to FIG. 17, the circular insulation material 141 is formed on the sidewall of the hole 13 so as to define a central hole. Then, the conductive metal 142 fills in the central hole so as to form the conductive via 14.

The subsequent steps of this embodiment are the same as the steps of FIGS. 11 to 13 so as to form the neural sensing devices 1 as shown in FIG. 1.

Referring to FIGS. 18 to 22, a method for making a neural sensing device according to another embodiment of the present invention is illustrated.

Figure 18:
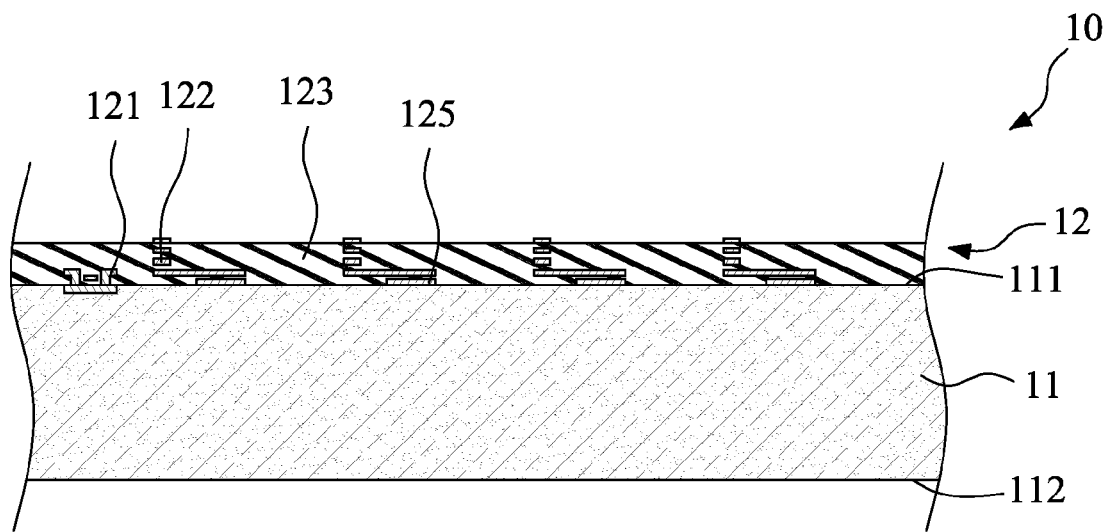
FIGS. 18 to 22 illustrate a method for making a neural sensing device according to another embodiment of the present invention.

Referring to FIG. 18, a wafer 10 is provided. The wafer 10 of this embodiment is the same as the wafer 10 of FIG. 4 except that the integrated circuit portion 12 of the wafer 10 of this embodiment further includes a plurality of bottommost pads 125 disposed on the active surface 111 of the base 11. Each of the bottommost pads 125 is electrically connected to the metal layers 122.

Figure 19:
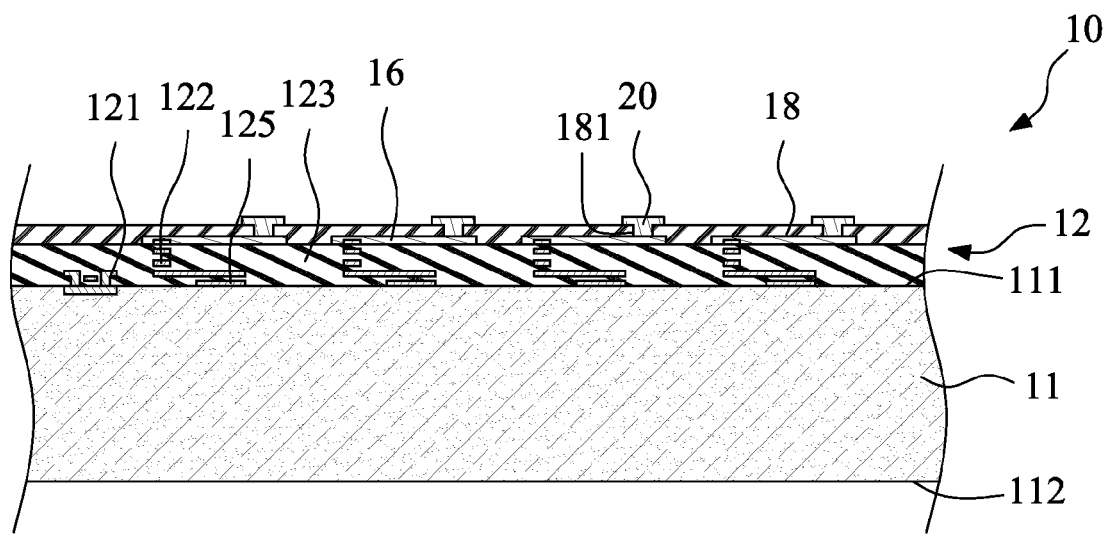

Referring to FIG. 19, the redistribution layers 16 are formed on the integrated circuit portion 12 to electrically connect the upmost layer of the metal layers 122. Then, the protection layer 18 is formed on the integrated circuit portion 12 to cover the first redistribution layers 16, wherein the protection layer 18 has a plurality of openings 181 to expose a part of each of the redistribution layers 16. Then, a plurality of under bump metallurgies (UBMs) 20 are formed on the protection layer 18 and in the openings 181 to electrically connect the redistribution layers 16.

Figure 20:
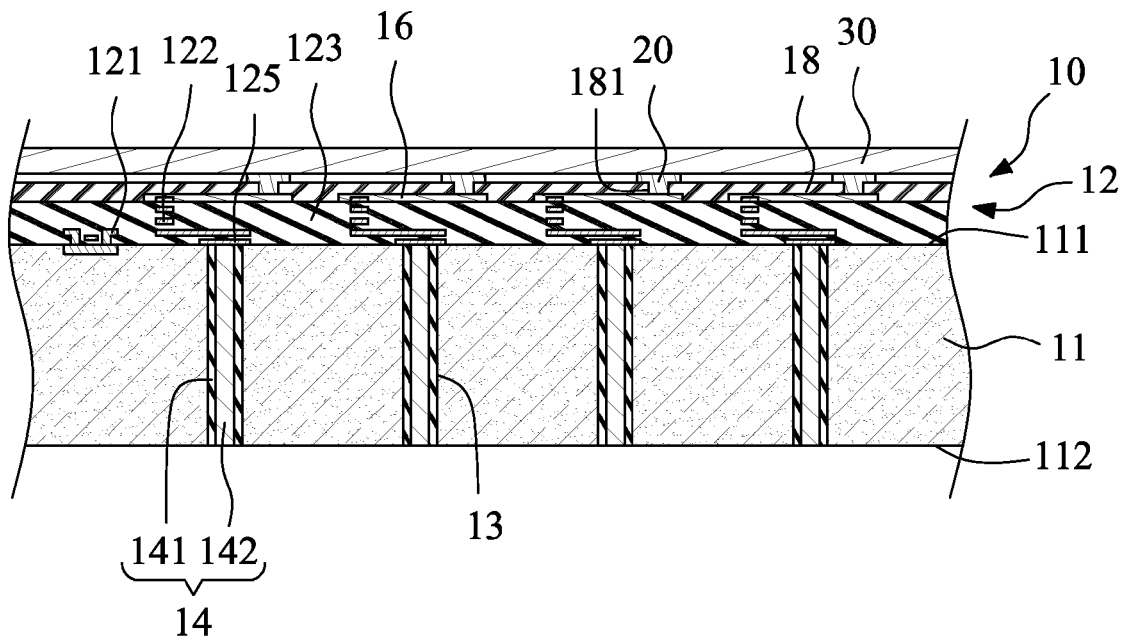

Referring to FIG. 20, the wafer 10 is attached to the carrier 30, wherein the under bump metallurgies (UBMs) 20 contact the carrier 30. Then, the base 11 is thinned from the backside surface 112 thereof by grinding. Then, the holes 13 are formed in the base 11 from the backside surface 112 of the base 11 by, for example, dry etching. The positions of the holes 13 correspond to that of the bottommost pads 125 of the integrated circuit portion 12 so as to expose the bottommost pads 125. In this embodiment, the depth of the hole 13 is about 240 µm to 280 µm, and the diameter of the hole 13 is about 60 µm. Then, the circular insulation material 141 is formed on the sidewall of the hole 13 so as to define a central hole. Then, the conductive metal 142 fills in the central hole so as to form the conductive via 14.

Figure 21:
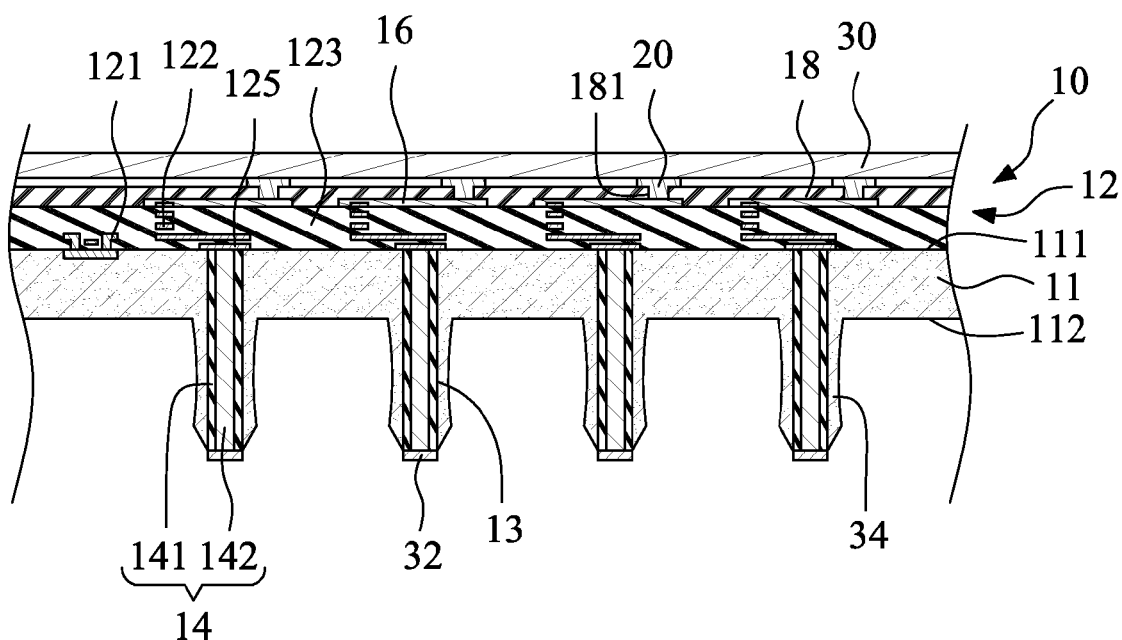

Referring to FIG. 21, a hard mask 32 is applied to the backside surface 112 of the base 11. The hard mask 32 has a pattern to cover the exposed conductive metal 142 of the conductive via 14, so that a part of the backside surface 112 of the base 11 is exposed. Then, the base 11 is selectively removed from the backside surface 112 by, e.g., etching. That is, the exposed part of the backside surface 112 that is not covered by the hard mask 32 is removed by, e.g., etching. Therefore, the probe bodies 34 are formed from the base 11 and protrude from the backside surface 112 of the base 11. Each of the conductive vias 14 is disposed in each of the probe bodies 34. In this embodiment, the height of the probe body 34 is at least about 150 µm, and the thickness of the remaining base 11 is at least about 200 µm.

Figure 22:
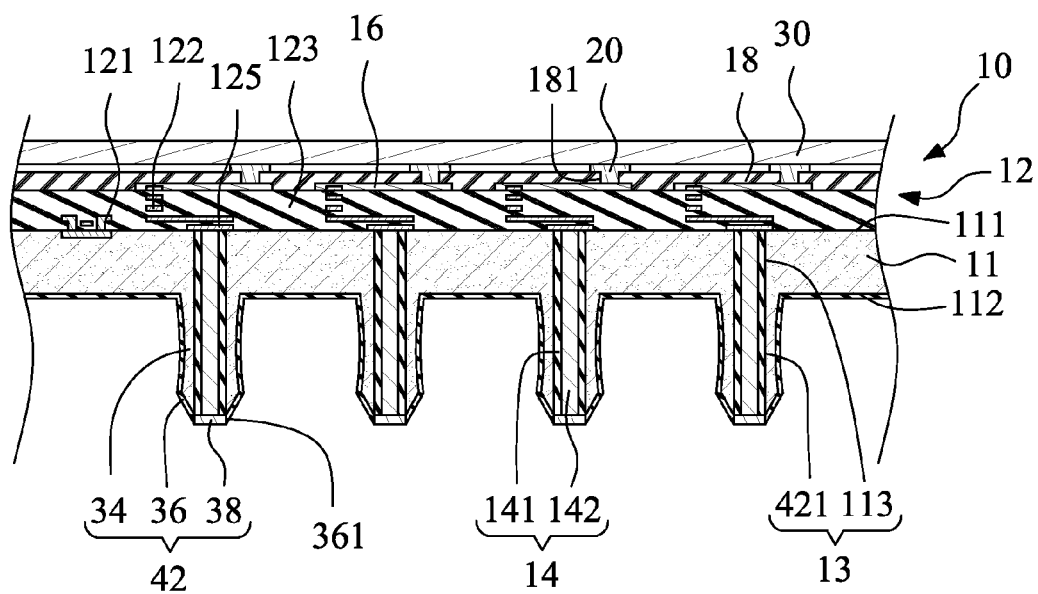

Referring to FIG. 22, the hard mask 32 is released so that the bottom end of the conductive metal 142 is exposed from the probe body 34. Then, the isolation layer 36 is formed on the probe bodies 34 and the backside surface 112. Then, the openings 361 are formed on the isolation layer 36 to expose the conductive metals 142 of the conductive vias 14. Then, the tip metals 38 are formed in the openings 361 of the isolation layer 36 by plating. Therefore, each of the tip metals 38 is formed on the conductive metal 142 of the conductive via 14, so as to contact the conductive metal 142 of the conductive via 14. Then, the wafer 10 is diced to form a plurality of neural sensing devices 1a as shown in FIG. 2.

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily be drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations are not limitations of the invention.

What is claimed is:

1. A neural sensing device, comprising:
    a base having an active surface and a backside surface;
    an integrated circuit portion disposed on the active surface of the base; and
    a plurality of microprobes protruding from the backside surface of the base, each of the microprobes having a conductive via disposed therein and electrically connected to the integrated circuit portion;
    wherein each of the microprobes has a probe body and an isolation layer, wherein the probe body protrudes from the backside surface of the base, the conductive via penetrates through the probe body, and the isolation layer covers the probe body and has an opening to expose a tip of the conductive via.

2. The neural sensing device of claim 1, wherein the conductive via penetrates through the base and the microprobe, extending from the active surface of the base to a tip of the microprobe.

3. The neural sensing device of claim 1, wherein a circular insulation material surrounds conductive metal of the conductive via.

4. The neural sensing device of claim 1, wherein the conductive vias are electrically isolated from each other.

5. The neural sensing device of claim 1, wherein the integrated circuit portion comprises at least one electrical element, a plurality of metal layers and at least one dielectric layer, the at least one electrical element is disposed adjacent to the active surface of the base and covered by the dielectric layer, and the metal layers are embedded in the dielectric layer.

6. The neural sensing device of claim 1, wherein the exposed tip is plated with platinum.

7. A neural sensing device, comprising:
    a base having an active surface and a backside surface;
    an integrated circuit portion disposed on the active surface of the base; and
    a plurality of microprobes, wherein each of the microprobes has a probe body, an isolation layer and a conductive via, wherein the probe body protrudes from the backside surface of the base, the conductive via is disposed in the probe body, and the isolation layer covers the probe body and has an opening to expose a plated tip of the conductive via.

8. The neural sensing device of claim 7, wherein the microprobes are structured to allow penetration into the stratum germinativum layer of human skin to collect bio-signals via the exposed tips of the conductive vias.

9. The neural sensing device of claim 8, wherein, when the microprobes penetrate the stratum germinativum layer, the microprobes are electrically insulated from the stratum corneum layer of the skin by the isolation layer.

10. The neural sensing device of claim 7, further comprising:
    a plurality of redistribution layers electrically connecting the integrated circuit portion and the conductive via;
    at least one protection layer covering the redistribution layers; and
    a plurality of under bump metallurgies (UBMs) disposed on the protection layer and electrically connected to the redistribution layers.

11. The neural sensing device of claim 10, wherein a tip of each of the conductive vias is exposed from the active surface of the base, and each of the redistribution layers contacts the exposed tip of each of the conductive vias.

12. The neural sensing device of claim 7, wherein the base and the probe body are made of the same semiconductor material.

* * * * *